(12) United States Patent
Kulkarni et al.

(10) Patent No.: US 7,943,167 B2
(45) Date of Patent: May 17, 2011

(54) COMPOSITIONS WITH HYDROPHILIC DRUGS IN A HYDROPHOBIC MEDIUM

(75) Inventors: Neema Kulkarni, Randolph, NJ (US); Kanji Meghpara, Morris Plains, NJ (US)

(73) Assignee: McNeil-PPC, Inc., New Brunswick, NJ (US)

( * ) Notice: Subject to any disclaimer, the term of this patent is extended or adjusted under 35 U.S.C. 154(b) by 249 days.

(21) Appl. No.: 11/391,518

(22) Filed: Mar. 28, 2006

(65) Prior Publication Data

US 2006/0222701 A1  Oct. 5, 2006

Related U.S. Application Data

(60) Provisional application No. 60/666,051, filed on Mar. 29, 2005.

(51) Int. Cl.
*A61K 9/48* (2006.01)

(52) U.S. Cl. ........................................................ 424/451

(58) Field of Classification Search .................. None
See application file for complete search history.

(56) References Cited

U.S. PATENT DOCUMENTS

| 5,362,564 | A | 11/1994 | Suzuki et al. | |
|---|---|---|---|---|
| 5,595,757 | A | 1/1997 | Kiefer et al. | |
| 5,795,590 | A | 8/1998 | Kiefer et al. | |
| 5,882,680 | A | 3/1999 | Suzuki et al. | |
| 5,888,538 | A | 3/1999 | Kiefer et al. | |
| 6,174,466 | B1 | 1/2001 | Kiefer et al. | |
| 6,228,397 | B1 * | 5/2001 | Shen et al. | 424/474 |
| 6,238,690 | B1 | 5/2001 | Kiefer et al. | |
| 6,361,298 | B1 | 3/2002 | Kiefer et al. | |
| 6,887,307 | B1 * | 5/2005 | Scott et al. | 106/205.01 |
| 2002/0013357 | A1 * | 1/2002 | Nadkarni et al. | 514/406 |
| 2003/0083354 | A1 * | 5/2003 | Kiel et al. | 514/352 |
| 2004/0052865 | A1 * | 3/2004 | Gower et al. | 424/687 |
| 2005/0079215 | A1 * | 4/2005 | Schleifenbaum et al. | 424/456 |
| 2005/0175651 | A1 * | 8/2005 | Simonnet et al. | 424/401 |

FOREIGN PATENT DOCUMENTS

| EP | 1025842 | | 8/2000 |
|---|---|---|---|
| EP | 1095651 | A2 * | 5/2001 |
| WO | 9611053 | | 4/1996 |
| WO | 9630115 | | 10/1996 |
| WO | 0006127 | | 2/2000 |
| WO | WO 0205788 | A1 * | 1/2002 |
| WO | 0243646 | | 6/2002 |
| WO | 03059503 | | 7/2003 |
| WO | 2005063209 | | 7/2005 |
| WO | 2005077521 | | 8/2005 |

* cited by examiner

*Primary Examiner* — Michael G Hartley
*Assistant Examiner* — Paul Dickinson
(74) *Attorney, Agent, or Firm* — Evan J. Federman

(57) ABSTRACT

In various embodiments of the present invention, a capsule is provided including a hydrophobic inner layer and at least one hydrophilic outer layer. The hydrophobic layer may include a hydrophilic component such as an active pharmaceutical ingredient (API) which may be fully encapsulated, partially encapsulated or part of an adsorption complex. Such capsules experience no or minimal cracking or breaking in the outer layer.

10 Claims, 2 Drawing Sheets

COMPOSITIONS WITH HYDROPHILIC DRUGS IN A HYDROPHOBIC MEDIUM

This application claims priority to U.S. Provisional Patent Application No. 60/666,051 filed Mar. 29, 2005.

FIELD OF THE INVENTION

The present invention relates to stable pharmaceutical compositions having an active pharmaceutical ingredient. More particularly, this invention relates to stable capsules with a hydrophilic component in a hydrophobic medium.

DESCRIPTION OF RELATED ART

Compositions in a capsule dosage form may include a fill material having one or more active agents dissolved or suspended in an appropriate liquid or paste vehicle, encapsulated in a gelatin shell, typically comprising gelatin together with a plasticizer. The fill material is typically a pumpable liquid or paste. The carrier for the fill material may be a single or a multi-component system that should be compatible with the outer gelatin phase(s) of the capsule.

Carrier mediums used in soft gelatin capsules fall into two general categories, hydrophilic and lipophilic. Unfortunately, hydrophilic carriers cannot be used in certain types of capsules such as when it may interact with the outer layers. Rather, in such capsules, hydrophobic or lipophilic carrier mediums need to be used. Typical examples include mineral oils (petroleum or petroleum-derived), vegetable oils (chiefly from seeds and nuts), animal oils (usually occurring as fats; the liquid types include fish oils), edible oils (chiefly vegetable oils as well as some special fish oils) and triglycerides (preferably short chain triglycerides). In some capsules with a hydrophobic carrier medium in a core phase, it has been observed that an outer shell material may crack and/or break thereby causing unacceptable leakage of the core material.

Accordingly, there is a need for a capsules containing hydrophilic compounds wherein the shell material does not crack or break.

SUMMARY

In several embodiments of the present invention, there is provided a capsule having a hydrophobic inner layer and at least one hydrophilic outer layer. The hydrophobic layer may include a hydrophilic component such as an active pharmaceutical ingredient (API) in a therapeutically effective amount. The API may be fully encapsulated, partially encapsulated or part of an adsorption complex. Such capsules experience minimal or no cracking or breaking in the at least one outer layer. Another embodiment of the present invention provides a seamless capsule having phenylephrine in a therapeutically effective amount. The phenylephrine may be fully encapsulated or partially encapsulated or adsorbed onto a complex.

Another embodiment of the present invention provides a package that may include a dispenser or blister package and a seamless capsule. A seamless capsule may include a hydrophobic inner layer and at least one hydrophilic outer layer. The hydrophobic layer may include a hydrophilic ingredient such as an active pharmaceutical ingredient (API) in a therapeutically effective amount. The API may be partially encapsulated, fully encapsulated or is part of an adsorption complex. The package may contain drug facts attached thereto.

Another embodiment of the present invention provides for a method of stabilizing a seamless capsule having a hydrophilic API in a hydrophobic inner layer. In one embodiment, there is provided a method of preventing or minimizing migration of a hydrophilic ingredient such as an API from a hydrophobic inner layer of a seamless capsule to an outer hydrophilic layer of a capsule by including the steps of providing an API in a therapeutically effective amount that is encapsulated, partially encapsulated or adsorbed and incorporating the API into the hydrophobic inner layer of a seamless capsule.

In various embodiments, there is provided a capsule including a hydrophobic inner layer and at least one hydrophilic outer layer. The hydrophobic inner layer may include a hydrophilic component. The hydrophilic component experiences no or minimal migration to the outer hydrophilic outer layer. The hydrophilic component may be an active pharmaceutical ingredient which may be present in a therapeutically effective amount.

DETAILED DESCRIPTION

In one embodiment of the present invention, there is provided a capsule having an encapsulated or partially encapsulated hydrophilic compound(s) in a hydrophobic carrier in an inner layer. Such capsules do not experience cracks or breaks in surrounding outer layer(s) that may have a hydrophilic carrier or phase. In another embodiment of the present invention, there is provided a seamless microcapsule with encapsulated or partially encapsulated hydrophilic APIs positioned in a hydrophobic carrier in an inner layer or phase and wherein the outer shell of the microcapsule does not experience breakage or cracking.

In several embodiments of the present invention, one useful capsule is a seamless capsule. Such seamless capsules typically include at least one inner layer, defined as the 'core layer' and at lease one outer layer, defined as a shell layer.

The terms microcapsule and minicapsule are synonymous with each other and used interchangeably throughout this specification.

Capsules may be formulated to disintegrate and/or dissolve directly in the buccal cavity or in the GI tract or stomach area. In various embodiments, one useful capsule includes a fast disintegrating capsule that disintegrates in the buccal cavity. In several embodiments of the present invention, a fast disintegrating capsule may be designed to disintegrate in the buccal cavity from about 1 second to about 60 seconds or from about 1 second to about 45 seconds or from about 1 second to about 30 seconds or from about 1 second to about 15 seconds. In one embodiment of the present invention, there is provided a seamless capsule that disintegrates in the buccal cavity between about 1 second and 30 seconds. In several embodiments, the capsule will disintegrate in the buccal cavity without any external forces such as biting on the capsule.

An embodiment of the present invention provides for a fast disintegrating capsule with a single inner hydrophobic core layer and a single hydrophilic outer layer, wherein the capsule is stable and does not experience any cracking or breaking in the outer layer. This type of capsule may be advantageous for several reasons. Depending on the materials utilized in the capsule, a capsule having multiple hydrophilic or water soluble outer layers may effect the desired disintegration performance of the capsule. For instance, a capsule with a hydrophobic core layer and two or more outer water soluble layers may not disintegrate as quickly as a capsule that has a single core layer and a single outer water soluble layer. Additionally, having a single core hydrophobic layer and a single outer water soluble layer may be advantageous from a manufacturing efficiency point of view.

Figure 1:
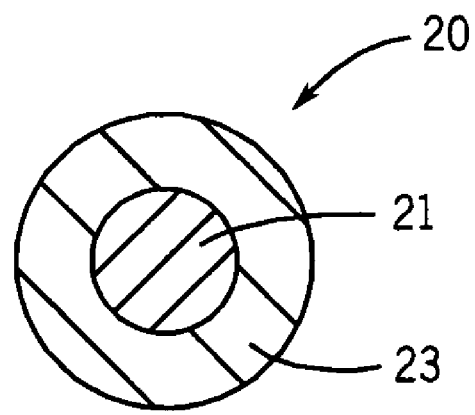
FIG. 1 is a cross section illustrating a capsule having an inner core layer and an outer shell layer as provided by one embodiment of the present invention.

An embodiment of the present invention is shown in FIG. 1, wherein a multilayered capsule includes an inner core layer and an outer shell layer. Other embodiments of the present invention include capsules with more layers such as an additional layer between the core and shell layer and/or an additional layer on the outside of the outer shell layer. Several embodiments of the present invention provide for a capsule that has 2, 3, 4, 5 phases or layers. The thickness of each layer may be adjusted by varying the ratio of the various solutions. Suitable enteric agents include pectin, alginic acid, cellulose such as carboxyl methylcellulose, celluloseacetate phthalate, and the like, Eudragit® which is one of an acrylic copolymer and the like and combinations thereof.

In various embodiments of the present invention, an API that resides in an inner core layer may be encapsulated or partially encapsulated by an appropriate means. Encapsulation of drugs is known to be useful for providing sustained release versions of certain APIs. While it may be desirable in certain circumstances to provide for a sustained release product so that API is released into the patient over an extended period of time, it would not be desirable to encapsulate a drug if an immediate release product is desired. In various embodiments of the present invention, there are provided capsules, such as seamless capsules that are designed to disintegrate in the buccal cavity. It has surprisingly been found that stable capsules can be provided by encapsulating or partially encapsulating the API contained therein.

Partially encapsulating an API is advantageous since it minimizes or eliminates the outer shell cracking issue while not creating an undesirable sustained release API. Another embodiment of the present invention also provides for a seamless capsule containing an encapsulated API wherein the encapsulated API is available for immediate release in the patient. In such embodiments, the encapsulation is in an effective amount to minimize or eliminate migration of the API to the outer shell. Alternatively, the encapsulation is in an effective amount to minimize or eliminate the deformations in the outer shell such as cracks, breaks and the like and combinations thereof. An API may be partially encapsulated, fully encapsulated, partial adsorbates, full adsorbates or combinations thereof.

While not wishing to be bound by any theory, it is believed that hydrophilic compounds, such as hydrophilic active pharmaceutical ingredients (APIs), tend to migrate from an inner layer or core phase which has a hydrophobic carrier medium to an hydrophilic phase located outside of the core or inner hydrophobic layer. In several embodiments, the hydrophilic phase or layer is an outer shell layer or a middle shell layer residing outside of the core hydrophilic phase or layer. While not wishing to be bound to any particular theory, it is believed that a partially or fully encapsulated or adsorbing an hydrophilic API reduces, minimizes or eliminates the API's affinity to migrate to an outer layer or phase, thereby reducing or eliminating the migration of the API to the outer shell and thereby reducing or eliminating the cracking or breaking of the outer shell.

Several embodiments of the invention contemplate that APIs can be encapsulated, partially encapsulated, adsorbed as a complex or partially adsorbed as a complex. Encapsulation can be achieved using conventional procedures and can be performed using water-insoluble as well as water-soluble agents. Alternatively, it is possible to encapsulate a release controlling substance, together with an API, within an encapsulating shell to provide for controlled release of a taste-masked capsule.

For instance, an API may be encapsulated or partially encapsulated by first granulating the API with a sufficient quantity of the desired encapsulation material. The wet mass is passed through a mesh screen such as a 10 mesh screen to break up any lumps, if necessary. The granules are dried over a forced air oven at 50° C. The dried powder is passed through a screen, such as a 40 mesh screen. The powder is then ready to be incorporated into the core inner solution.

Suitable materials that can be used to encapsulate or partially encapsulate an API include, but are not limited to, hydroxypropylcellulose, ethycellulose, hydroxypropylmethylcellulose (Aquacoat®), ethylcellulose, methacrylates, acrylic co-polymers such as Eudragit® (Butylmethacrylat-(2-Dimethylaminoethyl)methacrylat-Methylmethacrylat-Copolymer (1:2:1)"), KOLLICOAT®, polyvinylpyrrolidone and combinations thereof. The pharmaceutical composition can include other functional components presented for the purpose of modifying the physical, chemical or taste properties of the systemically active therapeutic agent. For example, the API can be in the form of a microencapsulation, ion-exchange resin complex, such as a sulfonated polymers, electro-chemical melt, supercritical fluids, magnesium trisilicate, coacervation, or cyclodextrin (cyclic-inked oligosaccharides) complexes. Useful sulphonated polymers include polystyrene cross-linked with 8% of divinylbenzene such as Amberlite® IRP-69 and IRP-64 (obtained by Rohm and Haas), Dow XYS-40010.00®, Dow XYS40013.00® (obtained from the Dow Chemical Company).

Various embodiments of the present invention provide for an outer layer that includes a water soluble layer. Useful materials for a water soluble outer, coating or shell layer include, but are not limited to, gelatins, proteins, polysaccharides, starches, celluloses and combinations thereof. Useful materials for the water soluble outer coating or shell layers include but are not limited to, albumin, pectin, guar gum, carboxymethyl starches, carboxymethyl celluloses, carrageenan, agar and the like, hydroxypropylcellulose, ethycellulose, hydroxypropylmethyl cellulose, such as Aquacoat®, polyvinyl alcohol, polyvinyl pyrrolidone, pullulan and combinations thereof. When the material for forming the coating layer contains protein or polysaccharide, useful amounts include an amount from about 100 parts by weight to about one part by weight. Other useful materials in the outer, coating or shell layer include an enteric material, a plasticizer, a preservative and a colorant and the like and combinations thereof.

To adjust the hardness of the shell, a material that increases the hardness of the shell material after hardening, such as sorbitol, can be added to the shell material along with the plasticizer. Furthermore, by adding a thickening polysaccharide, a gelling agent, a proteolytic agent or the like, it is possible to improve the long-term stability of the shell. The shell material can be colored to any arbitrary color tone by a pigment, and flavorings, sweeteners, souring agents or the like can be added. Sorbitol, thickening polysaccharides, gelling agents, proteolytic agents and the like are added at 10% by mass or less with respect to the total amount of the shell material, and preferably at 5% by mass or less.

Other useful materials in the water soluble phase include plasticizers, which include polyhydric alcohols, such as sorbitol, glycerin, polyethylene glycol and the like and combinations therof. A water-soluble polyvalent alcohol or water-soluble derivative thereof may also be used in water soluble outer or coating layer. Useful examples of polyvalent alcohol or water soluble derivatives thereof include but are not limited to, glycerin, polyglycerin, sorbitol, ethylene glycol, polyethylene glycol, propylene glycol, polypropylene glycol, ethylene oxide-propylene oxide copolymer, oligosaccharide, sugar ester, glyceride, sorbitan ester and the like. Useful preservatives and colorants include benzoic acid, para-oxybenzoate, caramel colorant, gardenia colorant, carotene colorant, tar colorant and the like and combinations thereof.

A film substance may be used on the water soluble outer or shell layer and may be formed by treating a capsule with a film forming substance. Suitable film formers include but are not limited to albumin, pectin, guar gum, carrageenan, agar and the like, hydroxypropylcellulose, ethycellulose, hydroxypropylmethyl cellulose, such as Aquacoat®, pullulan and combinations thereof.

Useful amounts of additives include 2 parts by weight to 98 parts by weight, based on 100 parts by weight of gelatin in the coating layer. In order to inhibit oxygen-permeability of the capsule of the present invention, sucrose may be contained in the coating layer, in addition to the film-forming material and additives. When sucrose is not contained in the coating layer, oxygen may permeate through the water-soluble gel layer to reach the content and oxidize the unsaturated fatty acid and derivative thereof during a long storage period of time. Oxidized unsaturated fatty acid and derivative thereof increase peroxide value (POV) and deteriorate product quality. Sucrose efficiently inhibits the disadvantage. Sucrose may be contained in an amount of one part by weight to 100 parts by weight based on 100 parts by weight of gelatin.

A water-soluble layer or phase may also contain an acid or an acid salt thereof, to minimize or prevent the capsule from insolubilizing. Useful acids or acid salt thereof include a water-soluble organic acid, an inorganic acid, or an acid salt thereof (for example, sodium salt). Suitable organic acid include acids having 2 to 6 carbon atoms, including, for example, citric acid, malic acid, tartar acid, fumaric acid, lactic acid, butyric acid, succinic acid and the like, an acid salt thereof (for example, sodium malate, potassium succinate, calcium citrate and the like); and combinations thereof. Useful inorganic acids include phosphoric acid, polyphosphoric acid, carbonic acid, an acid salt thereof (for example, dibasic sodium phosphate) and combinations thereof. Useful amounts of an acid or acid salt thereof to a water-soluble layer is generally from about 0.01 to about 50% by weight, or from about 0.05 to about 20% by weight, based on 100% by weight of a water soluble layer or phase.

The inner or core solution or phase of a capsule may include a fatty acid such as a unsaturated fatty acid or a derivative thereof. Suitable materials for the inner core include but are not limited to, vegetable fats and oils, animal fats and oils and mineral oils and combinations thereof. Suitable materials for the inner core include fish oils and a purified material thereof, liver oils, eicosapentaenoic acid (EPA), docosahexaenoic acid (DHA), arachidonic acid, prostaglandin and a derivative thereof, sucrose fatty acid ester, propylene glycol fatty acid ester, glycerin fatty acid ester, long chain fatty acid triglyceride, medium chain fatty acid triglyceride, ampho-ionic emulsifiers, lecithin, sesame oil, coffee oil, rapeseed oil, brown rice oil, liquid paraffin and combinations thereof.

To prepare an emulsified core liquid, well-known conventional methods can be used in which the main component, including an emulsifying agent, and an oil component are emulsified using a homogenizer to obtain an oil-in-water emulsion. Other useful materials for the core or inner phase include, but are not limited to, various types of a stabilizers for unsaturated fatty acid or a derivative thereof including antioxidants, such as vitamin E, vitamin C, β-carotene, eucalyptol, menthol, flavorings, sweeteners, wheat germ oil and the like and combinations thereof.

The core filler material can be in a liquid state when extruded from the multiple nozzle as the core liquid, and the core liquid can remain a liquid after the formation of the multilayer liquid drops, or alternatively can be a gel or solid after formation of the seamless capsule. The core material may include a foodstuff, health food, flavoring, condiments, pharmaceutical, aromatic agent, or the like, it is possible to include various additives such as solvents (for example, edible oils), sweeteners, souring agents, flavorings, colorings, thickeners (gelatinizing agents), stabilizers, and emulsifiers, or the like that are permitted in terms of food production or pharmacology. When the core material is prepared in a liquid state, it can take the form of a transparent solution, suspension, or a latex (cream) where the main component is dissolved in a solvent. The method in which a core liquid filler material is prepared can be any well-known method in the fields of food production or pharmaceutical manufacturing. For example, to prepare a transparent core liquid, the main component and additives are measured and mixed with a solvent such as a edible oil, and as needed heated and agitated to produce a uniform solution.

Useful amounts of the inner or core phase is from about 10% to 95% by weight, or from about 40% to about 90% by weight, based on the total weight of the capsule.

In several embodiments of the present invention, the seamless capsule may contain a viscous liquid which is scarcely miscible with water between an outer film and the inner or core phase. The viscous liquid which is scarcely miscible with water may be liquid having a viscosity of not more than 1000 cp at 100 C. Examples thereof include emulsifiers, oils, resins and the like and they may be used alone or in combination thereof. Examples of the emulsifier include nonionic emulsifiers having HLB value of 2 to 8 such as sucrose fatty acid ester, propylene glycol fatty acid ester, glycerin fatty acid ester (e.g. long chain fatty acid triglyceride, medium chain fatty acid triglyceride, such as NeoBee®, etc.), ampho-ionic emulsifiers such as lecithin or a mixture thereof. Examples of oils include vegetable fats and oils, animal fats and oils and mineral oil of which solubility in 100 g of absolute alcohol at 150 C is not more than 50 g, for example, sesame oil, coffee oil, rapeseed oil, brown rice oil, liquid paraffin and combinations thereof. Further, dl-alpha-tocopherol, isobutylene polymers (e.g. polybutylene, polybutene, etc.), resins (e.g. silicone resin, vinyl acetate resin, etc.), silicon dioxide, such as Cab-o-sil® and the like can be used. The viscous liquid may be present between the content and film in the case of producing the capsule. However, it is not necessarily required that the viscous liquid is present between the content and film, and it may be present in the content in the separate state.

The inner or outer layer may include other materials including APIs, foods, cosmetics, flavors, industrial chemicals and the like.

Another embodiment of the present invention provides for a seamless microcapsule with three layers, namely, the core layer, a middle layer and an outer shell layer. The middle layer may be added to the microcapsule by a third injection nozzle. The middle layer may provide for a more stable microcapsule. More particularly, the middle layer may provide for additional protection for the shell layer and prevent or minimize migration of the core layer to the outer shell layer.

An aspect of the present invention provides for a seamless capsule or capsule that includes an encapsulated or partially encapsulated API in a therapeutically effective amount. Useful APIs include antimicrobial agents, non-steroidal anti-inflammatory agents, antitussives, decongestants, anti-histamines, expectorants, anti-diaherrals, $H_2$-antagonists, proton pump inhibitors, analgesics, stimulants and combinations thereof. Useful APIs include diphenhydramine, dextromethorphan, phenylephrine, menthol, pseudoephedrine, acetaminophen, ibuprofen, famotidine, guaifenesin, ketoprofen, nicotine, celecoxib, valdecoxib, chlorpheniramine, fexofenadine, loratadine, desloratadine, cetirizine, ranitidine, simethicone, and isomers, pharmaceutically acceptable salts and prodrugs thereof and combinations thereof.

Further useful active pharmaceutical ingredients include diphenhydramine, dextromethorphan, phenylephrine, famotidine, ketoprofen, nicotine, valdecoxib, chlorpheniramine, loratadine, desloratadine, cetirizine, famotidine; simethicone, and isomers, pharmaceutically acceptable salts and prodrugs thereof and combinations thereof.

Useful amounts of phenylephrine include from about 1 milligram to about 60 mg, from about 1 mg to about 15 mg or from about 5 mg to about 10 mg or about 10 mg.

Various embodiments of the present invention provide compositions with at least two API's.

Useful API's include, but are not limited to:

(a) antimicrobial agents such as triclosan, cetylpyridium chloride, domiphen bromide, quaternary ammonium salts, zinc compounds, sanguinarine, fluorides, alexidine, octonidine, EDTA, and the like;

(b) non-steroidal anti-inflammatory and pain reducing agents such as aspirin, acetaminophen, ibuprofen, ketoprofen, diflunisal, fenoprofen calcium, flurbiprofen sodium, naproxen, tolmetin sodium, indomethacin, celecoxib, valdecoxib, parecoxib, rofecoxib and the like;

(c) antitussives such as benzonatate, caramiphen edisylate, menthol, dextromethorphan hydrobromide, chlophedianol hydrochloride and the like;

(d) antihistamines such as brompheniramine maleate, chlorpheniramine maleate, carbinoxamine maleate, clemastine fumarate, dexchlorpheniramine maleate, diphenylhydramine hydrochloride, azatadine maleate, diphenhydramine citrate, diphenhydramine hydrochloride, diphenylpyraline hydrochloride, doxylamine succinate, promethazine hydrochloride, pyrilamine maleate, tripelennamine citrate, triprolidine hydrochloride, acrivastine, loratadine, desloratadine, brompheniramine, dexbrompheniramine, fexofenadine, cetirizine, montelukast sodium and the like;

(e) expectorants such as guaifenesin, ipecac, potassium iodide, terpin hydrate and the like;

(f) analgesic-antipyretics such salicylates, phenylbutazone, indomethacin, phenacetin and the like;

(g) antimigraine drugs such as sumitriptan succinate, zolmitriptan, valproic acid eletriptan hydrobromide and the like;

(h) anti-gas and anti-diaherrals such as simethicone, loperimide, (i) $H_2$-antagonists, proton pump inhibitors such as ranitidine, famotidine, omeprazole and the like; and (j) central nervous system agents, The amount of the API's in the formulation may be adjusted to deliver a predetermined dose of the active agent over a predetermined period of time, which may typically vary from 4 to 24 hours. Examples of doses containing specific pharmaceutically active agents are set forth in Table 1.

TABLE 1

| Pharmaceutically Active Agent | Dose |
| --- | --- |
| Chlorpheniramine Maleate | 4-12 mg |
| Brompheniramine Maleate | 4 mg |
| Dexchlorpheniramine | 2 mg |
| Dexbrompheniramine | 2 mg |
| Triprolidine Hydrochloride | 2.5 mg |
| Cetirizine | 5-10 mg |
| Acrivastine | 8 mg |
| Azatadine Maleate | 1 mg |
| Loratadine | 5-10 mg |
| Dextromethorphan Hydrobromide | 10-30 mg |
| Ketoprofen | 12.5-25 mg |
| Sumatriptan Succinate | 35-70 mg |
| Zolmitriptan | 2.5 mg |
| Nicotine | 1-15 mg |
| Diphenhydramine Hydrochloride | 12.5-25 mg |
| Atorvastatin | 5-80 mg |
| Valdecoxib | 5-20 mg |
| Celecoxib | 5-20 mg |
| Rofecoxib | 5-25 mg |
| Ziprasidone | 20-80 mg |
| Eletriptan | 10-40 mg |

Except as otherwise noted, the amount of API is designated as % by weight per dosage form. Generally, the amount of the API used may be from about 0.01% to about 80% by weight, or from about 0.1% to about 40% by weight, or from about 1% to about 30% by weight, or from about 1% to about 10% by weight.

An "effective" amount or a "therapeutically effective amount" of an active ingredient refers to a non-toxic but sufficient amount of the agent to provide the desired effect. The amount of active agent that is "effective" will vary from subject to subject, depending on the age and general condition of the individual, the particular active agent or agents, and the like. Thus, it is not always possible to specify an exact "effective amount." However, an appropriate "effective" amount in any individual case can be determined by one of ordinary skill in the art using routine experimentation.

"Pharmacologically active" (or simply "active"), refers to a compound that has pharmacological activity and a "pharmacologically active" derivative of an active agent, refers to a derivative having the same type of pharmacological activity as the parent compound and approximately equal in degree. When the term "pharmaceutically acceptable" is used to refer to a derivative (e.g., a salt) of an active agent, it is to be understood that the compound is pharmacologically active as well. When the term "pharmaceutically acceptable" is used to refer to an excipient, it implies that the excipient has met the required standards of toxicological and manufacturing testing or that it is on the *Inactive Ingredient Guide* prepared by the Food and Drug Administration.

By "pharmaceutically acceptable" such as in the recitation of a "pharmaceutically acceptable excipient," or a "pharmaceutically acceptable additive," is meant a material that is not biologically or otherwise undesirable, i.e., the material can be incorporated into a pharmaceutical composition administered to a patient without causing any undesirable biological effects or interacting in a deleterious manner with any of the other components of the composition in which it is contained.

In various embodiments of the present invention, the dosage forms may be administered orally. Oral administration may involve swallowing, so that the composition with the API(s) enters the gastrointestinal tract, and/or buccal, lingual, or sublingual administration by which the API enters the blood stream directly from the mouth.

Useful inactive ingredients that may be included in the various phases or solutions of the capsule, may include but are not limited to, binding agents, filling agents, lubricating agents, suspending agents, sweeteners, flavorings and flavor enhancer agents, taste-masking agents, preservatives, buffers, wetting agents, anti-oxidants, colorants or coloring agents, pharmaceutically acceptable carriers, disintegrants, salivary stimulating agents, cooling agents, co-solvents (including oils), pH adjusting agents, effervescent agents, emollients, bulking agents, anti-foaming agents, surfactants, soluble organic salts, permeabilizing agents, glidants and other excipients and combinations thereof. Desirably, the agents are chemically and physically compatible with the API.

Examples of useful substantially water soluble carriers or filling agents include, but are not limited to, various starches, celluloses, carbohydrates compression sugars or soluble fillers. More particularly, useful fillers include but are not limited to lactose, lactose monohydrate, lactose anhydrous, sucrose, amylose, dextrose, mannitol, inositol, maltose, maltitol, sorbitol, glucose, xylitol, erythritol, fructose, maltodextrins; microcrystalline cellulose, calcium carboxy methyl cellulose; pregelatinized starch, modified starches, potato starch, maize starch; clays, including kaolin and polyethylene glycols (PEG) including PEG 4000; or combinations thereof. Useful amount of fillers include the range of about 1 to about 99 weight percent, or about 25 to about 95 weight percent or about 40 weight percent to about 95 weight percent of the compositions of this invention.

Compositions of the present invention may include a sweetener. Useful sweeteners include, but are not limited to, sugars such as sucrose, glucose (corn syrup), dextrose, invert sugar, fructose, and mixtures thereof; acid saccharin and its various salts such as the sodium or calcium salt; cyclamic acid and its various salts such as the sodium salt; the dipeptide sweeteners such as aspartame and alitame; natural sweeteners such as dihydrochalcone compounds; glycyrrhizin; Stevia rebaudiana (Stevioside); sugar alcohols such as sorbitol, sorbitol syrup, mannitol, xylitol and the like, synthetic sweeteners such as acesulfame-K and sodium and calcium salts thereof and other synthetic sweeteners, hydrogenated starch hydrolysate (lycasin); protein based sweetening agents such as talin (thaumaoccous danielli) and/or any other pharmacologically acceptable sweetener known by the state of the art, and mixtures thereof.

Suitable sugar alcohols useful as sweeteners include, but are not limited to, sorbitol, xylitol, mannitol, galactitol, maltitol, isomalt (PALATINIT™) and mixtures thereof. The exact amount of sugar alcohol employed is a matter of preference subject to such factors as the degree of cooling effect desired. Thus, the amount of sugar alcohol may be varied in order to obtain the result desired in the final product and such variations are within the capabilities of those skilled in the art without the need for undue experimentation.

In another embodiment, a capsule is free of sugar. A sugar-free formulation has the advantage that it can be administered easily to consumers with blood sugar disorders or to diabetics in need of such preparations. Such sweeteners include, but are not limited to, sucralose, acesulfame potassium, and aspartame which share properties such as absence of bitter and metallic aftertastes.

In another embodiment, a capsule may include acesulfame K, aspartame, sucralose and combinations thereof.

Acesulfame K is a commercial product of Nutrinova Nutrition Specialties & Food Ingredient GmbH. Useful amounts of sucralose in a dosage form is between about 0.002% to about 10% by total weight of the FDDF. However, this amount can vary greatly depending upon the nature of the composition being sweetened. In one preferred embodiment, the sweetener is a mixture of sucralose with acesulfame K.

One embodiment of the invention provides for a controlled or extended release composition.

Optionally, one or more flavors such as those described in U.S. Pat. No. 6,596,298 which is incorporated herein. Any amount of flavor can be used and will depend on characteristics of the active pharmaceutical ingredient(s); preferred concentration of flavoring is between about 0.01% to about 10% w/w of a composition.

Another embodiment of the present invention provides a kit having two or more separate compositions having an API in capsules, including seamless capsules, and a means for separately retaining said capsules, such as a container, divided bottle, or divided foil packet. An example of such a kit is the familiar blister pack used for the packaging of capsules and the like. Other embodiments contemplate articles of manufacture including various packaging configurations, ranging from unit dose blister packs to multiple dose packages such as bottles. To assist compliance, the kit may have directions for administration and may be provided with a so-called memory aid.

In one embodiment, capsules are provided in blister packaging which is believed to limit the amount of oxygen that may interact with the capsule and as such may also increase or enhance the stability of the drug product containing the API. Another embodiment contemplates a method of dispensing a capsule from a blister pack by forcing the drug product through a foil back on a blister pack.

An embodiment of the present invention provides a method for producing the encapsulated unsaturated fatty acid substance may be a conventional method for producing a soft capsule. An example of the method for producing the capsule includes a method containing steps of preparing a sheet for the coating layer mainly containing gelatin and a sheet for the water-soluble gel layer containing an acid or an acid salt thereof, respectively, laminating both sheets, drying to obtain a dried sheet and encapsulating unsaturated fatty acid or the derivative thereof as the content with the dried sheet on a rotary filler to form a seamed capsule; and another method for producing a seamless capsule by using an instrument equipped with some nozzles arranged concentrically.

Figure 2:
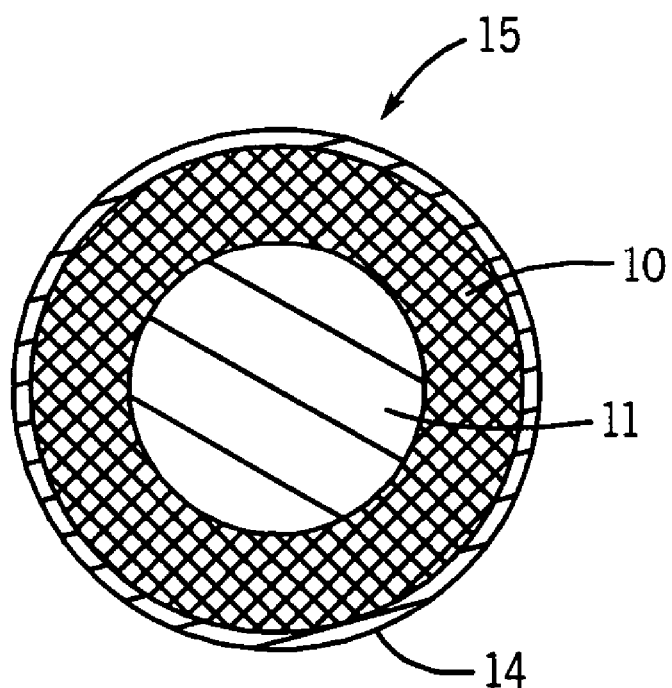
FIG. 2 is a cross section illustrating a capsule having an inner core layer and an outer coating layer and an outer film layer as provided by one embodiment of the present invention.

Seamless microcapsules may be manufactured by any acceptable machinery such as the seamless minicapsule production machine, such as the Spherex, manufactured by Freund Corp., Japan as shown in FIG. 2. Highly spherical uniform, seamless capsules may be produced by such machinery. A useful manufacturing process for seamless capsules, including seamless microcapsules, includes mixing the components of the core in one container and the components of the shell(s) in another container. The shell(s) materials are heated to provide a fluid medium. The core and shell(s) materials are then pumped separately to at least two fluid nozzles submerged in an organic carrier medium. The capsules formed are allowed to cooled and stiffen. They are then denatured and separated for further handling. Additional solutions may be injected to form a three or more system microcapsule. The core solution and the shell solution must be different. The principle of seamless minicapsule formulation is the utilization of surface tension. In particular, when two different solutions contact each other, surface tension works to reduce the contact area of the solution resulting in a spherical shape.

Suitable methods for producing seamless capsules are disclosed in U.S. Pat. No. 5,330,835 and U.S. Pat. No. 6,531,150, US 2004/0051192, U.S. Pat. No. 5,478,508 which are incorporated herein in their entirety.

FIG. 1 schematically shows a cross-sectional view of a capsule (20), with an inner core material (21) with a coating layer (23). FIG. 2 schematically shows a cross-sectional view of a capsule (15), with an inner core material (11), a coating layer (10) and a film layer (14).

Figure 3:
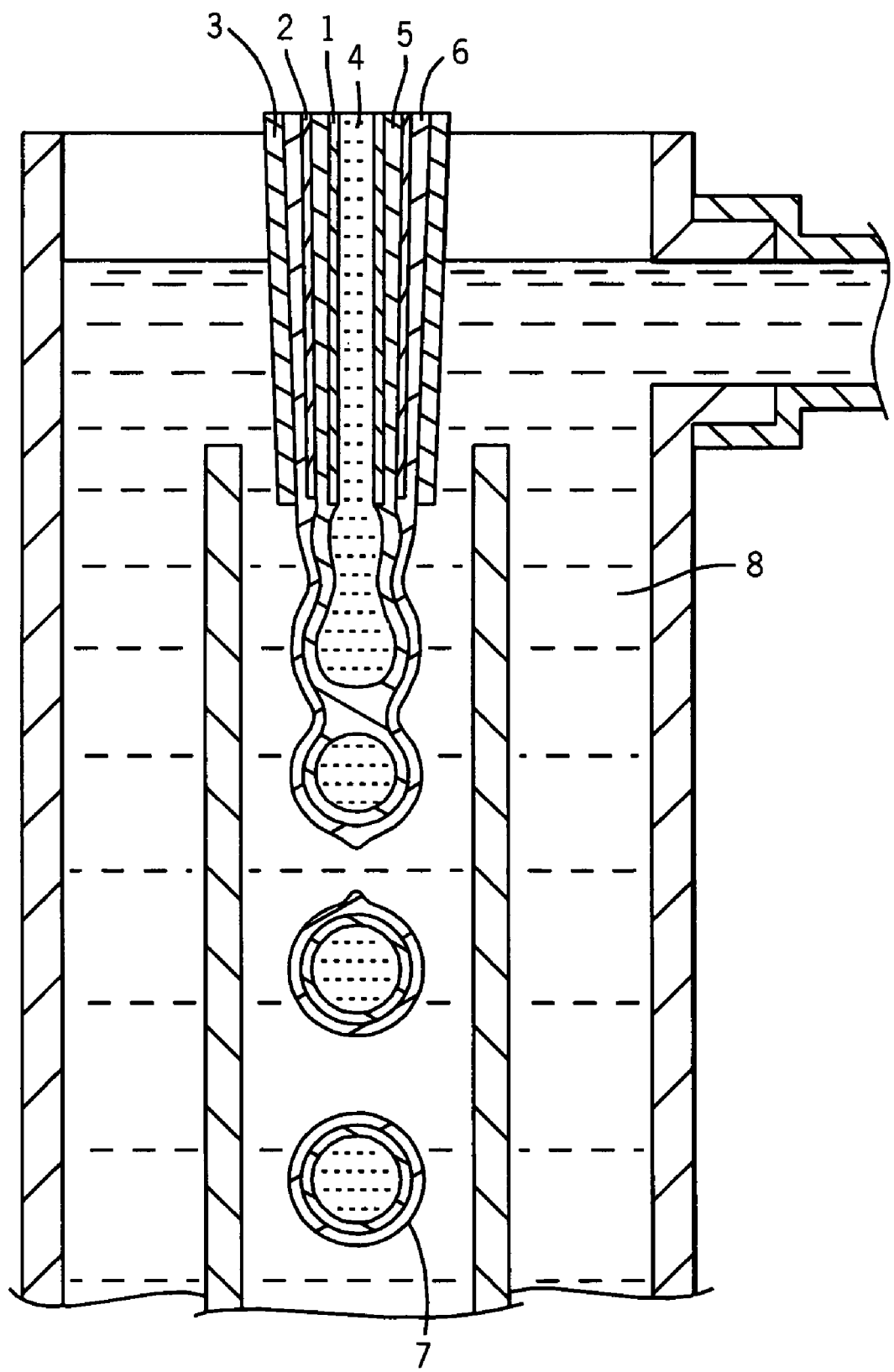
FIG. 3 is a schematic cross section illustrating one embodiment of the present invention of the nozzle part of an apparatus which is suitable for producing seamless capsules.

FIG. 3 is a schematic cross section illustrating one embodiment of the present invention which is suitable for producing a seamless capsule. The inner core material (4) of the capsule supplied to the nozzles is extruded from an annular end of an inner nozzle (called the first nozzle) (1), the material for forming the water-soluble gel layer (5) is extruded from an annular end of an intermediate nozzle (called the second nozzle) (2) and optionally a film-forming material for a coating layer (6) is extruded from an annular end of an outer nozzle (called the third nozzle) (3), simultaneously, to make a three-phase composite jet stream, followed by releasing the jet stream into a cooling solution (8) to obtain the encapsulated unsaturated fatty acid substance (7) of the present invention in a form of the seamless capsule.

In the method of the present invention, since all of the loading materials are liquid, the encapsulation process can be easily performed by adequately vibrating the jet stream with a vibration means to readily release the jet stream, and thereby a particle size of the resulting capsules may be controlled uniformly.

The encapsulated unsaturated fatty acid substance (7) produced by the method of the present invention may be used in any way of an undried form remaining moisture in the coating layer, or a dried form.

The capsule of the present invention may be formed into a desirable particle size of 0.1 mm to 20 mm, preferably 0.3 to 8 mm. The water-soluble outer layer (12) may have a thickness from about 0.001 to about 5.00 mm, or from about 0.01 to 1 mm.

EXAMPLES

TABLE 2

|  | Capsule 1% Target | Capsule 2% Target |
| --- | --- | --- |
| Outer Layer |  |  |
| Gelatin 200 B | 80.00% | 80.00% |
| Glycerol | 18.00% | 18.00% |
| Sorbitol | 2.00% | 2.00% |
| Purified Water | — | — |
| Weight of Outer Shell | 6 mg | 6 mg |
| Core Layer |  |  |
| trigliceride | 86.50% | 83.50% |
| sweetener | 1.50% | 1.50% |
| Cab-O-Sil | 1.00% | 1.00% |
| menthol | 3.50% | 3.50% |
| eucalyptol | 1.00% | 1.00% |
| phenylephrine HCl (encapsulated with ethylcellulose 53:47) | 5.00% |  |
| phenylephrine HCl (encapsulated with ethylcellulose 93:7) |  | 8.00% |
| Weight of Core Solution | 140 mg | 140 mg |
| Total Weight of Capsule | 146 mg | 146 mg |

The formulations in Table 2 are mixed to prepare the respective layers. The materials are extruded through each one of a double and triple nozzle, respectively, arranged concentrically and released into a cooling solution (vegetable oil) to produce capsules in form of a double and triple structure, respectively. The resulting capsules are spherical and about 8 mm in diameter.

TABLE 3

| Coating/Encapsulating Materials |
| --- |
| Ethylcellulose |
| Acrylic copolymer |
| Hydroxypropyl cellulose |

The API, phenylephrine, is partially encapsulated by granulating phenylephrine with the encapsulating materials listed in Table 3. The wet granulation mass is passed through a 10 mesh screen. The granules are dried over a forced air oven at 50° C. The dried powder is passed through a 40 mesh screen and the powder is then mixed into the core solution.

While the invention has been described in detail and with reference to specific examples thereof, it will be apparent to one skilled in the art that various changes and modifications can be made therein without departing from the spirit and scope thereof of the invention.

What is claimed is:

1. A capsule comprising a hydrophobic inner liquid core and at least one hydrophilic outer shell layer, said hydrophobic inner liquid core comprises a hydrophilic active pharmaceutical ingredient in a therapeutically effective amount mixed into said liquid core; said active pharmaceutical ingredient is fully encapsulated, partially encapsulated or part of an adsorption complex and said wherein said hydrophobic inner liquid core comprises a material selected from the group consisting of fish oils and a purified material thereof, liver oils, eicosapentaenoic acid, docosahexaenoic acid, arachidonic acid, sucrose fatty acid ester, propylene glycol fatty acid ester, glycerin fatty acid ester, long chain fatty acid triglyceride, medium chain fatty acid triglyceride, amphoionic emulsifiers, lecithin, sesame oil, coffee oil, rapeseed oil, brown rice oil, liquid paraffin and combinations thereof wherein said pharmaceutical ingredient is phenylephrine encapsulated, partially encapsulated or adsorbed with a material selected from the group consisting of cellulose, sulphonated polymers, acrylic co-polymers, trisilicates, polystyrenes, cyclodextrins and combinations thereof.

2. The capsule according to claim 1, wherein said capsule is a seamless capsule.

3. The capsule according to claim 2, wherein said capsule has a diameter from about 2 mm to about 10 mm.

4. The capsule according to claim 1, wherein said at least one hydrophilic outer shell layer is a single layer.

5. The capsule according to claim 1, wherein said capsule disintegrates in the buccal cavity between about 1 and 30 seconds.

6. The capsule according to claim 1, wherein said active pharmaceutical ingredient is encapsulated or partially encapsulated with an acrylic copolymer.

7. The capsule according to claim 1, wherein the ratio of the encapsulation or adsorption material to active pharmaceutical ingredient is from about 10 to 1 to 1 to 10.

8. The capsule according to claim 1, wherein the ratio of the encapsulation or adsorption material to active pharmaceutical ingredient is from about 3 to 1 to 1 to 3.

9. The capsule according to claim 1, wherein said at least one hydrophilic outer shell layer comprises a material selected from the group consisting of albumin, pectin, guar gum, carboxymethyl starch, carboxymethyl cellulose, carrageenan, agar, hydroxypropylcellulose, ethycellulose, hydroxypropylmethyl cellulose, polyvinyl alcohol, polyvinyl pyrrolidone, pullulan and combinations thereof.

10. The capsule of claim 1, wherein said phenylephrine is encapsulated, partially encapsulated or adsorbed with a material selected from the group consisting of hydroxypropylcellulose, ethycellulose, hydroxypropylmethylcellulose, methacrylates, butylmethacrylat-(2-dimethylaminoethyl) methacrylat-methylmethacrylate-copolymer (1:2:1), polyvinylpyrrolidone, magnesium trisilicate, polystyrene cross-linked with 8% of divinylbenzene and combinations thereof.

* * * * *